US005691375A

United States Patent [19]

Behounek et al.

[11] Patent Number: 5,691,375
[45] Date of Patent: Nov. 25, 1997

[54] METHOD FOR PREVENTING OR REDUCING RISK OF ONSET OF CARDIOVASCULAR EVENTS EMPLOYING AN HMG COA REDUCTASE INHIBITOR

[75] Inventors: Bruce D. Behounek, Yardley; Mark E. McGovern, Philadelphia, both of Pa.; Adeoye Y. Olukotun, Hopewell, N.J.

[73] Assignee: Bristol-Myers Squibb Company, Princeton, N.J.

[21] Appl. No.: 448,211

[22] Filed: May 23, 1995

Related U.S. Application Data

[62] Division of Ser. No. 182,471, Jan. 18, 1994.
[51] Int. Cl.$^6$ .................................................. A61K 31/21
[52] U.S. Cl. ................................................................ 514/510
[58] Field of Search ................................................ 514/510

[56] References Cited

U.S. PATENT DOCUMENTS

| | | | |
|---|---|---|---|
| 4,346,227 | 8/1982 | Terahara et al. | 560/119 |
| 4,920,123 | 4/1990 | Beyer | 514/255 |
| 5,008,284 | 4/1991 | Grover et al. | 514/423 |

FOREIGN PATENT DOCUMENTS

| | | |
|---|---|---|
| 0219782 | of 0000 | European Pat. Off. . |
| 0461548A2 | 12/1991 | European Pat. Off. . |

OTHER PUBLICATIONS

Schettler, G., "The role of diet and drugs in lowering serum cholesterol in the postmyocardial infarction patient," Cardiovasc. Drugs, Ther., 1989, 2/6 (795–799).
Glatter, T.R., "Hyperlipidemia. What is 'normal', who should be treated and how," Postgrad. Med., 1984, 76/7 (49–50).
Satler, L.F., et al, "Reduction in coronary heart disease: Clinical and anatomical considerations," Clin. Cardiol., 1989, 12/8 (422–426).
Wilhelmsen, L., "Practical Guidelines for drug therapy after myocardial infarction," Drugs, 1989, 38/6 (1000–1007).
Yamamoto, A., et al, "Clinical features of familial hypercholesterolemia," Arteriosclerosis, Jan.–Feb. 1989, 9 (1 Suppl.) pp. I66–74.
Goldstein, J. L., et al, "The LDL receptor defect in familial hypercholesterolemia. Implications for pathogenesis and therapy," Med. Clin. North Am., 1982, 66/2 (335–362).

Tsujita, Y. "A Potent HMG–CoA Reductase Inhibitor, Pravastatin Sodium–Tisue–Selective Inhibition of Cholesterolgenesis and Preventive Effect on Atherosclerosis in WHHL Rabbits," J. Drug Dev. 1990:3 (Suppl. 1), 155–159.
Maher, V.M., et al, "Analysis of Evidence from Cholesterol–Lowering and Regression Trials," J. Drug Dev. 1990:3 (Suppl. 1), 199–203.
Lewis, B. "On lowering lipids in the post–infarction patient," Journal of Internal Medicine 1991; 29:483–488.
"A Coronary Primary Prevention Study of Scottish Men Aged 45–64 Years: Trial Design," J. Clin Epidemiol vol. 45, No. 8 pp. 849–860, 1992.
Goldman, L., et al, "Projected Cost–Effectiveness of Lovastatin for Cholesterol Reduction," Clin. Res. 36, No. 3, 337A, 1988).
Sacks, F.M. et al, "Rationale and Design of a Secondary Preventon Trial of Lowering Normal Plasma Cholesterol Levels After Acute Myocardial . . . Recurrent Events Trial (CARE)", Am. J. Card vol. 68, Dec. 1, 1991, pp. 1436–1446.
Fuster, V., et al, "Atherosclerotic Plaque Rupture and Thrombosis," Suppl. II, Circulation, vol. 82, No. 3, Sep. 1990, II–47–II59.
Crouse, J.R., et al, "Pravastatin, Lipids, and Atherosclerosis in the Carotid Arteries: Design Features of a Clinical Trial with Carotid Atherosclerosis Outcome," Controlled Clinical Trials 13:495–506 (1992).
Edelman, S., et al, "Hyperkalemia During Treatment with HMG–CoA Reductase Inhibitor," New Engl. J. of Med., vol. 320, No. 18, May 4, 1989, pp. 1219–1220.
Pitt, B., et al, "design and Recruitment in the United States of a Multicenter Quantitative Angiographic Trial of Pravastatin to Limit Atherosclerosis in the Coronary Arteries (PLAC I)", Amer. J. Card., vol. 72, Jul. 1, 1993, pp. 31–35.
"Effects of Pravastatin in Patients with Serum Total Cholesterol Levels from 5.2 to 7.8 mmol/liter (200 to 30 mg/dl) Plus Two Additional Atherosclerotic Risk Factors," Am. J. Card., Nov. 1, 1993, pp. 1031–1037.
Pearson, T.A., et al, "The Rapid Reduction in Cardiac Events with Lipid–Lowering Therapy: Mechanisms and Implications," Am. J. Card., vol. 72, Nov. 1, 1993, pp. 1072–1073.

Primary Examiner—Theodore J. Criares
Attorney, Agent, or Firm—Burton Rodney

[57] ABSTRACT

A method is provided for preventing or reducing the risk of onset of a cardiovascular event by administering an HMG CoA reductase inhibitor such as pravastatin, to a patient which has one or more risk factors for a coronary and/or cerebrovascular event such as hypercholesterolemia.

6 Claims, 1 Drawing Sheet

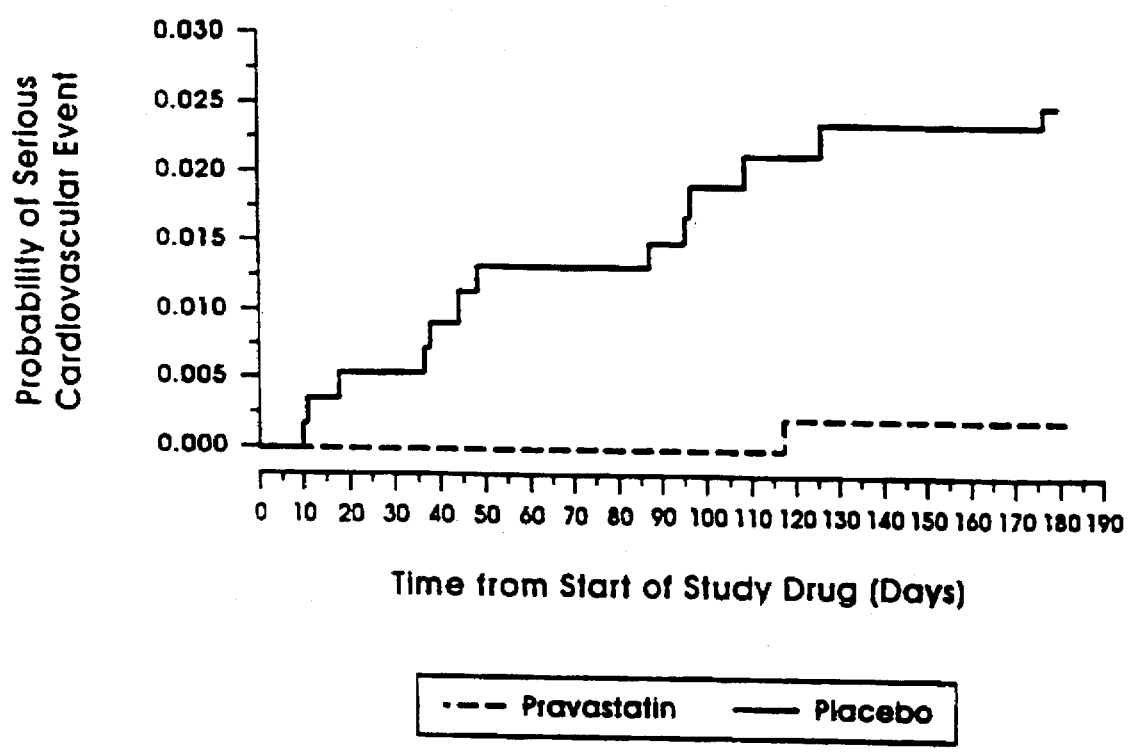
FIGURE

METHOD FOR PREVENTING OR REDUCING RISK OF ONSET OF CARDIOVASCULAR EVENTS EMPLOYING AN HMG COA REDUCTASE INHIBITOR

This is a division of application Ser. No. 08/182,471, filed Jan. 18, 1994, still pending.

FIELD OF THE INVENTION

The present invention relates to a method for preventing or reducing the risk of or onset of cardiovascular events employing an HMG CoA reductase inhibitor, such as pravastatin.

BACKGROUND OF THE INVENTION

Despite significant progress in reducing mortality due to atherosclerotic coronary artery disease (CAD) over the last several years, cardiovascular disease remains the major cause of death in most developed countries. The relation between CAD and elevated concentrations of serum total cholesterol, particularly low-density lipoprotein (LDL) cholesterol, is well documented.

It is well established that lipid disorders are important factors in the development of coronary heart disease (CHD), Schettler, G., "The role of diet and drugs in lowering serum cholesterol in the postmyocardial infarction patient," Cardiovasc. Drugs Ther., 1989, 2/6 (795–799).

Glatter, T. R., "Hyperlipidemia. What is 'normal', who should be treated and how," Postgrad. Med., 1984, 76/6 (49–59), states that "As the Coronary Primary Prevention Trial has recently shown, a 1% reduction in cholesterol level produces a 2% reduction in risk of myocardial infarction."

Goldstein, J. L., et al, "The LDL receptor defect in familial hypercholesterolemia. Implications for pathogenesis and therapy," Med. Clin. North Am., 1982, 66/2 (335–362) indicate that "familial hypercholesterolemia was the first genetic disorder recognized to cause myocardial infarction. To this day, it remains the outstanding example of a single gene mutation that causes both hypercholesterolemia and coronary atherosclerosis."

Satler, L. F., et al, "Reduction in coronary heart disease: Clinical and anatomical considerations," Clin. Cardiol., 1989, 12/8 (422–426) disclose that "the higher the total plasma cholesterol and low density lipoprotein cholesterol (LDL-C), the greater the risk that coronary artery disease will develop. Recently, clinical trials including the Coronary Drug Project, the Lipid Research Clinics Coronary Primary Prevention Trial (LRC-CPPT), and the Helsinki Heart Study provided evidence that lowering cholesterol reduces the frequency of fatal and nonfatal coronary events." In addition, Satler et al disclose that other studies "demonstrated that lowering of cholesterol was associated with a decreased incidence of progression of coronary disease, as well as with the potential for reduction in the atherosclerotic plaque."

Wilhelmsen, L., "Practical guidelines for drug therapy after myocardial infarction," Drugs, 1989, 38/6 (1000–1007) discloses that it is advisable to correct blood lipid disturbances in effective management of the postinfarction patient.

Yamamoto, A., et al, "Clinical features of familial hypercholesterolemia," Arteriosclerosis, Jan.-Feb. 1989, 9 (1 Suppl.) p I66–74, disclose that "in addition to the low density lipoprotein (LDL) cholesterol level, higher triglyceride and lower high density lipoprotein (HDL) cholesterol levels correlate with an increased risk of ischemic heart disease.

Other references disclosing the relation between CAD and elevated concentrations of serum total cholesterol include 1. Canner P. L. et al, "Fifteen year mortality in Coronary Drug Project patients: long-term benefit with niacin", J. Am. Coll. Cardiol. 1986; 8:1245–1255.
2. Frick, M. H. et al, "Helsinki Heart Study: primary-prevention trial with gemfibrozil in middle-aged men with dyslipidemia. Safety of treatment, changes in risk factors, and incidence of coronary heart disease," N. Engl. J. Med. 1987; 317:1237–1245.
3. Kannel, W. B. et al, "Serum cholesterol, lipoproteins, and the risk of coronary heart disease: the Framingham Study," Ann. Intern. Med. 1971; 74:1–12.
4. "The Lipid Research Clinics Program. The Lipid Research Clinics Coronary Primary Prevention Trial results, I: reduction in incidence of coronary heart disease," JAMA 1984; 251–351–364.
5. Martin, M. J. et al, "Serum cholesterol, blood pressure, and mortality: implications from a cohort of 361,662 men," Lancet 1986; 2:933–936.

Efforts to further reduce the mortality rate from CAD should benefit from appropriate screening for, and treatment of, hypercholesterolemia. Primary hypercholesterolemia is initially treated with a low-cholesterol low-fat diet and lifestyle modification. If these measures are inadequate, lipid lowering drugs are then added. Agents currently available for the treatment of hypercholesterolemia include bile acid-binding resins, nicotinic acid, probucol, fibrates, and 3-hydroxy-3-methylglutaryl coenzyme A reductase inhibitors. Pravastatin, a member of the latter class, in doses up to 40 mg/day, reduces serum LDL cholesterol an average of 32 to 34% and total cholesterol an average of 24 to 26% in patients with primary hypercholesterolemia. Hunninghake, D. B. et al, "Efficacy and safety of pravastatin in patients with primary hypercholesterolemia, I: a dose-response study." Atherosclerosis 1990; 85:81–89.

DESCRIPTION OF THE INVENTION

In accordance with the present invention, surprisingly and unexpectedly, it has been found that patients with one or more risk factors for a coronary and/or cerebrovascular event such as hypercholester-olemia, who are treated an HMG CoA reductase inhibitor, such as pravastatin, experience a rapid marked and significant reduction in cardiovascular events. Thus, although a certain number of patients having one or more risk factors for coronary or cerebrovascular events are expected to suffer a cardiovascular incident, such as a myocardial infarction and/or unstable angina, it has unexpectedly been found that such patients when treated with an HMG CoA reductase inhibitor, such as pravastatin, have a rapid and sizable reduction in such cardiovascular events. What is even more remarkable is the fact that such reduction in cardiovascular events occur within one year and usually within 6 months of treatment and even sooner. This is especially significant inasmuch as until now it has been the generally held view that a treatment effect on cardiac event rates appears only after a lag phase of $\geq 2$ years, as seen in the Coronary Primary Prevention Trial (JAMA 1984; 251:351–364) and the Helsinki Heart Study (N. Engl. J. Med. 1987; 317:1237–1245).

Thus, in accordance with the present invention, a method is provided for preventing onset of or reducing risk of a cardiovascular event in a patient having one or more risk factors for a coronary and/or cerebrovascular event wherein a therapeutically effective amount of an HMG CoA reductase inhibitor, preferably pravastatin, lovastatin, simvastatin and fluvastatin, more preferably pravastatin, is administered systemically, such as orally or parenterally.

The term "risk factors for a coronary and/or cerebrovascular event" as employed herein refers to risk factors such as hypercholesterolemia, coronary artery disease (CAD), family history of coronary artery disease, hypertension, diabetes, cigarette smoking, cerebrovascular disease and/or male gender.

The term "coronary artery disease" (CAD) as employed herein refers to diseases including atherosclerosis of the coronary arteries, previous myocardial infarction, angina pectoris and/or heart failure.

The term "cerebrovascular disease" as employed herein refers to diseases including atherosclerosis of the intracranial and/or extracranial arteries, stroke, and transient ischemic attacks.

The term "cardiovascular event(s)" or "serious cardiovascular adverse event(s)" as employed herein refers to coronary and/or cerebrovascular event(s) including primary myocardial infarction, secondary myocardial infarction, angina pectoris (including unstable angina), congestive heart failure, sudden cardiac death, cerebral infarction, syncope, transient ischemic attack and the like.

In accordance with the method of the invention, where the risk factor in patients to be treated is hypercholesterolemia, the serum total cholesterol concentrations will be at least 5.2 mmol/liter (at least 200 mg/dl). The patients may also have other risk factors for atherosclerotic coronary artery disease such as hypertension, previous myocardial infarction, smoker and the like.

Notwithstanding the above, it will be appreciated that in accordance with the present invention, the HMG CoA reductase inhibitor may be administered to patients irrespective of cholesterol levels and other risk factors to achieve the rapid reduction in cardiovascular events.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, velostatin (synvinolin or simvastatin) and related compounds as disclosed in U.S. Pat. Nos. 4,448,784 and 4,450,171, with pravastatin, lovastatin or simva-statin being preferred. Other HMG CoA reductase inhibitors which may be employed herein include, but are not limited to, fluvastatin, fluindostatin (Sandoz XU-62-320), pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl) alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other HMG CoA reductase inhibitors.

In addition, phosphinic acid compounds useful in inhibiting HMG CoA reductase suitable for use herein are disclosed in U.S. Pat. No. 4,904,646, which compounds have the moiety

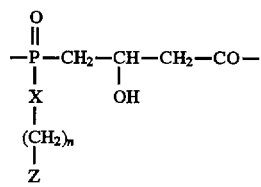

wherein X is —O— or —NH—, n is 1 or 2 and Z is a hydrophobic anchor.

Another class of HMG CoA reductase inhibitors suitable for use herein include phosphinic acid compounds disclosed in U.S. Pat. No. 5,091,378, which compounds have the moiety

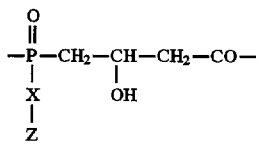

wherein X is —CH$_2$—, —CH$_2$—CH$_2$—, —CH=CH—, —CH$_2$CH$_2$CH$_2$—, —C≡C— or —CH$_2$O—, where O is linked to Z, and z is a hydrophobic anchor.

Most preferred is pravastatin.

The above-mentioned U.S. patents are incorporated herein by reference.

In carrying our the method of the present invention, the HMG CoA reductase inhibitor may be administered to mammalian species, such as dogs, cats, humans, etc., and as such may be incorporated in a conventional systemic dosage form, such as a tablet, capsule, elixir or injectable. The above dosage forms will also include the necessary carrier material, excipient, lubricant, buffer, anti-bacterial, bulking agent (such as mannitol), anti-oxidants (ascorbic acid or sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the HMG CoA reductase inhibitor in dosages employed, for example, for pravastatin, lovastatin and simvastatin as indicated in the Physician's Desk Reference, such as in an amount within the range of from about 1 to 2000 mg, per day in single or divided doses, and preferably from about 4 to about 200 mg per day in single or divided doses.

A preferred oral dosage form, such as tablets or capsules, will contain the HMG CoA reductase inhibitor in an amount of from about 0.5 to about 100 mg, preferably from about 5 to about 80 mg, and more preferably from about 10 to about 40 mg.

Tablets of various sizes can be prepared, e.g., of about 1 to 2000 mg in total weight, containing the active substance in the ranges described above, with the remainder being a physio-logically acceptable carrier or other materials according to accepted pharmaceutical practice. These tablets can, of course, be scored to provide for fractional doses. Gelatin capsules can be similarly formulated.

Liquid formulations can also be prepared by dissolving or suspending active substances in a conventional liquid vehicle acceptable for pharmaceutical administration so as to provide the desired dosage in one to four teaspoonsful.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for a cardiovascular event remains or the symptoms continue. Sustained release forms of such formulations which may provide such amounts biweekly, weekly, monthly and the like may also be employed. A dosing period of at least one to two weeks or until hypercholesterolemia and/or atherosclerosis has regressed are required to achieve minimal benefit.

DESCRIPTION OF THE FIGURE

The accompanying FIGURE is a graph of life-table analysis of serious cardiovascular adverse events during 26 weeks of treatment with pravastatin or placebo in 1,062 patients with primary hypercholesterolemia.

The following Examples represent preferred embodiments of the invention.

EXAMPLE 1

A pravastatin formulation in the form of tablets having the following composition was prepared as described below.

| Ingredient | Parts by Weight |
| --- | --- |
| Pravastatin | 7 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg, 10 mg, 20 mg or 40 mg pravastatin which may be used in preventing or reducing risk of a cardiovascular event such as a primary or second myocardial infarction, angina, stroke, TIA, and the like.

EXAMPLE 2

Pravastatin tablets are prepared employing conventional pharmaceutical techniques containing 20 mg pravastatin and inert ingredients employed, namely microcrystalline cellulose, providine, lactose, magnesium stearate and croscarmellose sodium as described in the 1993 PDR.

EXAMPLE 3

The pravastatin tablets may be employed to prevent or reduce risk of a cardiovascular event in accordance with the present invention.

Lovastatin tablets are prepared employing conventional pharmaceutical techniques containing 20 mg lovastatin, cellulose, color, lactose, magnesium stearate and starch and butylated hydroxyanisole as a preservative as described in the 1993 PDR.

The lovastatin tablets may be employed to prevent or reduce risk of a cardiovascular event in accordance with the present invention.

EXAMPLE 4

Simvastatin tablets are prepared employing conventional pharmaceutical techniques containing 20 mg simvastatin, cellulose, color, lactose, magnesium stearate, hydroxypropyl cellulose, hydroxypropyl methyl cellulose, iron oxides, talc, titanium dioxide and starch and butylated hydroxyanisole as a preservative as described in the 1993 PDR.

The simvastatin tablets may be employed to prevent or reduce risk of a cardiovascular event in accordance with the present invention.

EXAMPLE 5

This example describes a large multinational study, "Effects of Pravastatin in Patients with Serum Total Cholesterol Levels from 5.2 to 7.8 mmol/liter (200 to 300 mg/dl) Plus Two Additional Atheroscle-rotic Risk Factors," The Pravastatin Multinational Study Group for Cardiac Risk Patients, reported in Am. J. Cardiology Vol. 72, Nov. 1, 1993, 1031–1036. The study was designed to examine the efficacy and safety of pravastatin, together with diet modification and advice on smoking, in patients with primary hypercholesterolemia and $\geq 2$ additional risk factors for coronary artery disease (CAD).

METHODS

Study Design and Procedures

The efficacy and long-term safety of pravastatin in hypercholesterolemic patients were investigated in this multicenter, randomized, double-blind, placebo-controlled trial. After dietary stabilization and recommendations for lifestyle modification during a 6-week placebo lead-in period, patients were randomized to receive pravastatin 20 mg or placebo at bedtime. After 13 weeks, patients who responded (defined as a decrease in total cholesterol level by >15% from baseline or to <5.2 mmol/liter [200 mg/dl]) to treatment continued on the same study medication for 13 additional weeks. Patients who failed to achieve this therapeutic response were to have their dose of medication doubled for the next 13 weeks. Compliance with dietary instructions and other lifestyle counseling were periodically assessed. After completing the initial 26-week period, patients were given the option to continue in an additional 26-week double-blind phase and, following the first 52 weeks, a final 26-week period that was open-label for pravastatin in patients originally assigned to that treatment group. Additional lipid-lowering medications, except other 3-hydroxy-3-methylglutaryl coenzyme A reductase inhibitors and fibrates, could be added to patients not meeting treatment goals at the end of the first 26 weeks. Fibrates could be added in the open-label period of the study in patients originally assigned placebo.

The protocol was approved by each local ethics committee, and patients gave informed consent before randomization.. The study population was to be limited to men and postmenopausal or surgically sterile women 20 to 69 years old. At entry, patients were to have a serum total cholesterol concentration between 5.2 and 7.8 mmol/liter (200 and 300 mg/dl) despite dietary intervention as well as $\geq 2$ additional risk factors for CAD as defined in the protocol (male gender, systemic hypertension, cigarette smoking, family history of CAD, prior myocardial infarction, or history of angina pectoris). Exclusion criteria included (1) a history of homozygous familial hypercholesterolemia; (2) types I, III, IV or V hyperlipoproteinemia; (3) significant metabolic, renal, hepatic or endocrine disease; (4) history of drug abuse; or (5) obesity (>40% above ideal body weight). Patients were also excluded if, within 8 weeks of randomization, they were taking cortico-steroids, immunosuppressive drugs, investigational drugs, androgens, or estrogens and progestins for indications other than replacement therapy. Other lipid-lowering treatment had to be discontinued $\geq 8$ weeks before randomization.

After $\geq 4$ weeks of dietary stabilization, 2 qualifying blood samples for the lipid profile were drawn approximately 1 week apart after an overnight fast of $\geq 10$ hours. Seated systolic and diastolic blood pressures were recorded at 2 weeks and 1 week before randomization; other risk factors were assessed 1 week before randomization. Baseline lipid and laboratory safety tests, blood pressure and body weight measurements, and an ophthalmologic evaluation (including visual acuity and determination of lenticular opacities) were performed at randomization. The presence of concurrent disease and the use of concomitant medications were also recorded. When patients returned for clinic visits at weeks 6, 13 and 26, body weight and blood pressure were measured, morning samples for lipid profiles and laboratory safety tests were drawn, and clinical adverse events and concomitant medications were recorded. Drug compliance (by tablet count) was assessed and the ophthalmologic evaluation was repeated at weeks 13 and 26.

Laboratory Evaluations

Lipid analyses were performed at local laboratories and a central laboratory. Local laboratory lipid evaluations, including serum total cholesterol, high-density lipoprotein (HDL) cholesterol and triglycerides were to be performed on all subjects at weeks 0, 6, 13 and 26. Total cholesterol was also to be measured between weeks 10 and 12 before dose adjustments at week 13. The LDL cholesterol concentration was calculated using the Friedewald equation converted to mmol/liter: LDL cholesterol=total cholesterol−(0.45 triglycerides HDL cholesterol). Central laboratory lipid evaluations were also to be performed on all subjects at weeks 0, 13 and 26 for serum total cholesterol and triglycerides to corroborate the results from the local laboratories.

Laboratory safety tests were performed by local laboratories and consisted of hematology (hemoglobin, red blood cell count, hematocrit, platelet count, and white blood cell count and differential) and blood chemistries (urea, creatinine, uric acid, calcium, total bilirubin, alkaline phosphatase, aspartate aminotransferase, alaninc aminotransferase, 7-glutamyl aminotrans-ferase, total protein, albumin and creatine kinase).

Statistical Methods

To assess the comparability of treatment groups, baseline values and demographic characteristics for all randomized patients were summarized for each treatment group by descriptive statistics. The primary efficacy variables were the serum lipids analyzed at local laboratories at weeks 0, 6, 13 and 26. All values were transformed to natural logarithms for the analysis. Geometric means were used to summarize lipid values by treatment group at each visit. Treatment groups were compared by analysis of covariance of change from baseline in transformed values with baseline as a covariate.

The incidence of adverse events in each treatment group was summarized by body system and individual events. In addition, events predefined by the protocol to be serious, e.g., fatal events or events leading to or prolonging hospitalization, were tabulated. Hematology and biochemistry variables were summarized and analyzed by geometric means and analysis of covariance of change from baseline. Ophthalmologic results were summarized in terms of the number of lenticular opacities present at base-line and at weeks 13 and 26. Visual acuity (without correction) results were summarized in terms of number of patients who improved, worsened, or did not change from baseline to weeks 13 and 26. Differences in the incidence of adverse events were typically analyzed by the chi-square test with the Fisher's exact test used for rare events. Results were reported as statistically significant if a 2-sided p value $\leq 0.05$ was attained.

RESULTS

Patient Disposition and Baseline Characteristics

Data are reported for 1,062 patients from 89 sites in 8 countries as of a datalock date. During the initial 26-week double-blind treatment period, 530 patients received pravastatin and 532 received placebo. The first 26-week phase was completed by 946 patients (89.1%); 111 patients (10.5%) discontinued the study drug or were lost to follow-up, and termination data were not available for 5 patients (0.5%). Of the 111 discontinued patients, 50 (45%) received pravastatin and 61 (55%) received placebo. Patients were discontinued for the following reasons: adverse events (n=58), inclusion/exclusion criteria not met (n=29), lost to follow-up (n=16), inadequate efficacy (n=1), and other, nonadverse event-related causes (n=7). Of the 53 patients withdrawn for reasons other than adverse events, 25 (47%) received pravastatin and 28 (53%) received placebo. Patients who discontinued because of adverse events are discussed in the section describing safety results.

TABLE I

Summary of Demographic and Baseline Characterisstics of Randomized Patients

| | Pravastatin 20 mg (n = 530) | Placebo (n = 532) |
|---|---|---|
| Age (years) | | |
| Mean | 55 | 55 |

TABLE I-continued

Summary of Demographic and Baseline Characterisstics of Randomized Patients

|  | Pravastatin 20 mg (n = 530) | Placebo (n = 532) |
|---|---|---|
| Range | 20–86 | 22–77 |
| Sex (no. [%] of patients) | | |
| Male | 410 (77) | 403 (76) |
| Female | 119 (23) | 128 (24) |
| Data not available | 1 (0.2) | 1 (0.2) |
| Total cholesterol (mmol/L)* | | |
| Mean | 6.74 | 6.77 |
| Range | 5.1–10.1 | 3.5–10.3 |
| Cardiac risk factors (no. [%] of patients) | | |
| Hypertension | 251 (47) | 253 (48) |
| Family history of CAD | 234 (44) | 226 (42) |
| Cigarette smoking | 147 (28) | 158 (30) |
| Previous myocardial infarction | 172 (32) | 194 (36) |
| Angina pectoris† | 198 (37) | 231 (43) |

*Qualifying local laboratory value for entrance into the study (mean of last 2 values before baseline); n = 528 for pravastatin, and n = 530 for placebo.
†p <0.05.
CAD = corona artery disease.

Baseline characteristics and the number of CAD risk factors were generally similar in the 2 groups (Table I). Most of the patients had either 2 or 3 additional CAD risk factors—436 (82%) in the pravastatin group and 441 (83%) in the placebo group. Four or 5 additional risk factors were present in 86 patients (16%) in each group. Contrary to protocol specifications, 6 patients taking pravastatin (1.1%) and 4 taking placebo (0.8%) with only 1 additional CAD risk factor were included in the study. The number of risk factors was unknown for 2 patients (0.4%) in the pravastatin group and 1 patient (0.2%) in the placebo group. The treatment groups were comparable in the prevalence of CAD risk factors except for history of angina, which was more prevalent in the placebo group ($p<0.05$).

Effects on Plasma Lipids

At week 13, patients treated with pravastatin had significant reductions in LDL cholesterol (26%), total cholesterol (19%) and triglycerides (12%) ($p <0.001$ compared with placebo), and significant elevations in HDL cholesterol (7%) ($p<0.001$ compared with placebo). At that time, 66% (326 of 491) of the patients taking pravastatin had achieved the target cholesterol goal versus 7% (34 of 485) of the patients taking placebo. Efficacy was maintained at 26 weeks (Table II). In the placebo group, plasma lipid concentrations did not change appreciably during the 26 weeks. The response rate at week 26 was similar to that seen at week 13. The dose of blinded therapy was increased to 40 mg at bedtime at week 13 in 31% of pravastatin-treated patients and in 81% of placebo-treated patients. At week 26, the average dose in pravastatin-treated patients was 26.5 mg. Eighty-one percent of patients taking pravastatin achieved an LDL cholesterol level $\leq 4.1$ mmol/liter (160 mg/dl) and 47% attained an LDL cholesterol concentration of $\leq 3.4$ mmol/liter (130 mg/dl) at week 26. Central laboratory results were similar and supported the results from the local laboratories.

TABLE II

Effect of Treatment on Lipid Concentrations at Week 26

| Lipids | No. | Pravastatin Mean ± SEM (mmol/L) | No. | Placebo Mean ± SEM (mmol/L) | Between-Treatment p Value |
|---|---|---|---|---|---|
| LDL cholesterol* | | | | | |
| Baseline | 499 | 4.69 ± 1.05 | 510 | 4.66 ± 1.09 | |
| Week 26 | 459 | 3.47 ± 0.74 | 458 | 4.66 ± 0.92 | |
| % Change | | −26.01 | | 0.00 | <0.001 |
| Total cholesterol | | | | | |
| Baseline | 521 | 6.81 ± 0.78 | 529 | 6.87 ± 0.83 | |
| Week 26 | 483 | 5.55 ± 0.82 | 468 | 6.86 ± 0.91 | |
| % Change | | −18.50 | | −0.15 | <0.001 |
| Triglycerides | | | | | |
| Baseline | 520 | 1.77 ± 0.82 | 525 | 1.86 ± 0.86 | |
| Week 26 | 483 | 1.56 ± 0.74 | 468 | 1.84 ± 0.86 | |
| % Change | | −11.86 | | −1.08 | <0.001 |
| HDL cholesterol | | | | | |
| Baseline | 500 | 1.14 ± 0.35 | 510 | 1.15 ± 0.39 | |
| Week 26 | 459 | 1.23 ± 0.37 | 458 | 1.18 ± 0.35 | |
| % Change | | 7.90 | | 2.61 | <0.005 |

*Calculated according to the following formula: LDL cholesterol − (0.45 triglycerides + HDL cholesterol) in mmol/liter.
HDL = high-density lipoprotein; LDL = low-density lipoprotein.

Clinical Safety

In the first 26 weeks, there were no differences between the pravastatin and placebo treatment groups in total incidence of clinical adverse events. Adverse events were reported in 120 of 530 pravastatin-treated patients (22.6%) and 129 of 532 placebo-treated patients (24.2%). However, significantly more cardiovascular clinical adverse events were reported in the placebo group (29, 5.5%). than in the pravastatin group (15, 2.8%) ($p<0.05$). Likewise, serious adverse events were reported significantly more often in patients receiving placebo. Six of these events occurred in 5 pravastatin-treated patients (0.9%) and 26 occurred in 25 placebo-treated patients (4.7%) ($p<0.001$; Table III). One patient receiving pravastatin had 2 serious adverse events (acute symptoms of gallbladder disease and peripheral arterial occlusion) unrelated to each other, as did 1 patient receiving placebo (unstable angina and cerebral infarction). Serious cardiovascular adverse events (predefined as those that were fatal or required or prolonged hospitalization), the most dominant category of serious adverse events, were reported in 1 pravastatin-treated patient (0.2%) and in 13 placebo-treated patients (2.4%) ($p<0.001$; Table III). A life-table analysis of serious cardiovascular adverse events is shown in the accompanying FIGURE. Myocardial infarction (fatal and nonfatal), as reported by the study sites, occurred in 6 patients taking placebo (1.1%) and in no patient taking pravastatin ($p=0.031$) during this period. A similar pattern was present for reported cases of unstable angina leading to hospitalization (Table III). There was also 1 sudden cardiac death, presumed due to massive myocardial infarction, in the placebo group. The differences between the treatment groups in the incidence of serious cardiovascular events and myocardial infarction in the first 26 weeks remained significant in multivariate analyses that accounted for prior myocardial infarction and history of angina pectoris present at baseline. In addition, there were 4 serious cerebrovascular events (1 case of transient ischemic attack and 3 cerebrovascular accidents) in the placebo group, compared with none in the pravastatin group. Three placebo-treated patients died during the first 26 weeks of this study from cardiovascular-related causes (2 from fatal myocardial infarctions and 1 from sudden cardiac death), whereas no pravastatin-treated patient died during this period.

TABLE III

| Serious Adverse Events During the First 26 Weeks | | |
|---|---|---|
| | Pravastatin 20 mg (n = 530) | Placebo (n = 532) |
| Cardiovascular | | |
| Myocardial infarction | 0 | 6* |
| Unstable angina | 0 | 5 |
| Acute congestive heart failure | 1 | 1 |
| Sudden cardiac death | 0 | 1 |
| Subtotal | 1 | 13† |
| Central nervous system | | |
| Cerebral infarction | 0 | 3 |
| Syncope | 0 | 1 |
| Transient ischemic attack | 0 | 1 |
| Subtotal | 0 | 5 |
| Surgery | | |
| Coronary artery bypass graft | 0 | 3‡ |
| Abdominal (hernia) | 0 | 1 |
| Breast | 0 | 1 |
| Joint (knee) | 1 | 0 |
| Subtotal | 1 | 5 |
| Other | | |
| Pulmonary | 0 | 3 |
| Gastrointestinal | 2 | 0 |
| Diabetes | 1 | 0 |
| Peripheral arterial disease | 1 | 0 |
| Subtotal | 4 | 3 |
| Total of all serious adverse events | 6 | 26§ |

*$p = 0.031$ by Fisher's exact test; when prior myocardial infarction and history of angina were introduced as covariates, the statistical results remained significant using logistic regression; includes 4 nonfatal myocardial infarctions and 2 fatal myocardial infarctions.
†$p <0.001$ by chi-square test; when prior myocardial infarction and history of angina were introduced as covariates, the statistical results remained significant using logic regression.
‡Includes 2 elective procedures and 1 procedure performed for ischemic cardiomyopathy.
§$p <0.001$ by chi-square test.

Twenty-five of the pravastatin-treated (4.7%) and 33 of the placebo-treated (6.2%) patients were withdrawn from the study in the first 26 weeks because of an adverse event. One patient taking pravastatin was withdrawn after 5 days of double-blind therapy because of angioedema thought to be possibly related to drug therapy, and another patient taking pravastatin was withdrawn from the study because of increased liver function test values (alanine aminotransferase, aspartate aminotrans-ferase and 7-glutamyl aminotransferase) considered by the investigator to be unrelated to double-blind treatment. Three pravastatin-treated and 3 placebo-treated patients were withdrawn because of creatine kinase elevation or musculoskeletal events. Of the 3 pravastatin-treated patients, 1 discontinued therapy because of an asymptomatic increase in creatine kinase, from 340 to 446 U/liter, and 2 because of muscle aches or musculoskeletal pain without creatine kinase changes. Three placebo-treated patients were withdrawn from the study because of musculoskeletal adverse events (myalgia, musculoskeletal pain and muscle strain) not accompanied by elevations in creatine kinase.

Evaluation of the ophthalmologic results showed that changes in visual acuity measurements (without correction) and the incidence of new ocular opacities were limited and similar in the 2 treatment groups.

During the subsequent 52-week long-term portion of the study (during which other lipid-lowering agents could be added), clinical adverse events were reported in 55 of 297 pravastatin-treated (18.5%) and 49 of 221 placebo-treated (22.2%) patients. Five pravastatin (1.7%) and 6 placebo (2.7%) patients withdrew because of adverse events. Only 1 adverse event (diarrhea) was thought to be related to pravastatin administration. One pravastatin-treated and 2 placebo-treated patients sustained myocardial infarctions, whereas 1 case of unstable angina was reported in the pravastatin group and 3 additional cases of unstable angina were reported in the placebo group. During the entire 78-week study, there were 9 myocardial infarctions, 8 in the placebo group and 1 in the pravastatin group ($p=0.038$), and 9 episodes of unstable angina, 8 in the placebo group and 1 in the pravastatin group ($p=0.038$). There were no deaths in either treatment group during the long-term portion of the trial.

Laboratory Safety Evaluations

Protocol-defined laboratory abnormalities of liver function tests and muscle enzyme levels were infrequently seen. One placebo-treated (0.2%) and 6 pravastatin-treated (1.1%) patients had transient, asymptomatic elevations of hepatic transaminases to >3 times the upper limit of normal. Elevations of creatine kinase values to >4 times pretreatment values occurred in 14 patients taking pravastatin (2.6%) and in 8 taking placebo (1.5%). The elevations were not associated with musculoskeletal symptoms and did not lead to discontinuation of double-blind treatment. The syndrome of drug-induced myopathy (myalgia associated with increase in creatine kinase level to >10 times upper limits of normal) was not observed in any patient treated with pravastatin in this trial. As previously described, 1 pravastatin-treated patient was removed from the study at week 6 because of an asymptomatic increase in creatine kinase which had been elevated at baseline.

During the first 26 weeks, patients randomized to pravastatin demonstrated increases from baseline in mean levels of alanine aminotransferase (16.02 to 17.27 U/liter), aspartate aminotransferase (17.24 to 19.29 U/liter) and creatine kinase (70.62 to 76.36 U/liter) at the end of treatment. Differences between the 2 treatment groups in mean percent change from baseline for all 3 parameters were significant ($p<0.05$) at 1 or more time points during the initial double-blind treatment period, although the magnitude of the increases in the pravastatin group was small (3 to 12%) and not clinically significant.

DISCUSSION

In this study, treatment with pravastatin, 20 to 40 mg once daily (average dose 26.5 mg) resulted in significant reductions in levels of total and LDL cholesterol (19 and 26%, respectively) and trigly-cerides (12%), and an increase in HDL cholesterol concentrations (8%) at the end of the initial 26 weeks. Significantly fewer serious cardiovascular events (Table III) were observed among patients receiving pravastatin during this initial double-blind treatment period.

Although this trial was not designed to examine the effects of pravastatin on clinical cardiac end points, a marked reduction in the number of serious cardiovascular adverse events was observed in the pravastatin-treated group. This finding is in contrast to the generally held view that a treatment effect on cardiac event rates appears only after a lag phase of ≧2 years, as seen in the Coronary Primary Prevention Trial and the Helsinki Heart Study.

SUMMARY

This placebo-controlled, multinational study evaluated the use of pravastatin in 1,062 patients with hypercholesterolemia (serum total cholesterol concentrations of 5.2 to 7.8 mmol/liter [200 to 300 mg/dl]) and ≧2 additional risk factors for athero-sclerotic coronary artery disease. Efficacy and safety analyses were performed on the initial 26-week, randomized, double-blind, placebo-controlled period; further safety analyses were conducted on the subsequent 52 weeks, which included an additional 26-week double-blind phase permitting other lipid-lowering agents and a final 26-week open-label period. At 13 weeks, pravastatin at a dose of 20 mg once daily at bedtime significantly lowered serum low-density lipoprotein cholesterol 26% (4.7 to 3.5 mmol/liter [182 to 135 mg/dl]), total cholesterol 19% (6.8 to 5.6 mmol/liter [263 to 217 mg/dl]) and triglycerides 12% (1.8 to 1.6 mmol/liter [159 to 142 mg/dl]) ($p<0.001$ compared with placebo) and significantly raised serum high-density lipoprotein cholesterol 7% (1.1 to 1.2 mmol/liter [43 to 46 mg/dl]) ($p<0.001$ compared with placebo). Efficacy of pravastatin was maintained at 26 weeks, and during this initial period there were significantly more serious cardiovascular adverse events in the placebo group (13 events, 2.4%) than in the pravastatin group (1 event, 0.2%) ($p<0.001$). Six myocardial infarctions, 5 cases of unstable angina and 1 sudden cardiac death occurred in the placebo group, compared with none of these events in the pravastatin group. In this study, pravastatin produced beneficial effects on serum lipids and was associated with a reduction in the incidence of serious cardiovascular adverse events. (Am. J. Cardiology 1993;72:1031–1037).

Pearson, T. A. et al, (apparently affiliated with Columbia University), "The Rapid Reduction in Cardiac Events with Lipid-Lowering Therapy: Mechanisms and Implications," Am. J. Cardiology Vol. 72, Nov. 1, 1993, pp 1072–1073 in commenting on the clinical trial described above stated as follows:

"In this issue of The American Journal of Cardiology, the Pravastatin Multinational Study Group reports the results of a randomized, placebo-controlled, double-blinded study, that examined the safety and efficacy of pravastatin (2 to 40 mg/day). The study included 1,062 patients with moderate hypercholesterolemia and ≧2 additional risk factors. A sizable number of subjects had symptomatic coronary disease as 1 risk factor. Pravastatin lowered low-density lipoprotein (LDL) and increased high density lipoprotein (HDL) cholesterol levels, with high levels of tolerability but without major side effects.

"These results may be expected from an HMG-CoA reductase inhibitor, now well established as a safe and effective means to lower serum LDL cholesterol levels. More striking, however, was the rapid and sizable reduction in cardiovascular events. Although the study was not designed to measure cardiovascular events, the occurrences of these events were collected as part of an overall review of clinical adverse conditions. Although the definitions of myocardial infarction and unstable angina are not fully described in the manuscript, the study was placebo-controlled and double-blinded, suggesting that the clinical events should have been assessed similarly in both treatment and control arms. Over the 78 weeks of the study, 16 cases of myocardial infarction or unstable angina were observed in the placebo group versus 2 in the pravastatin arm. Remarkably, the greatest reduction in events appeared in the first 26 weeks of the study. In fact, summing up the medical and surgical events in the coronary and cerebrovascular beds (Table III [IV SIC]), there were 21 such events in the placebo group versus only 1 in the pravastatin group! The somewhat serendipitous nature of these findings merits comment as to the biological plausibility of such an observation and its clinical implications.

"The implications of such a large and relatively acute reduction in cardiac events are manifold. First, an increase in attention to serum lipids and lipoproteins in patients at high risk for disease seems indicated, including diagnostic and therapeutic considerations of the patient's LDL cholesterol as part of the comprehensive treatment of those with a new diagnosis of coronary disease consistent with recent recommendations. (LaRosa, J. C., et al, 'Cholesterol lowering as a treatment for established coronary heart disease,' Circulation 1992; 82:1229–1235). The magnitude of the reduction of cardiac events observed in this study exceeds those of interventions such as aspirin and β blockers that are now generally recognized as cornerstones of postmyocardial infarction therapy. Second, such an acute reduction should tip the cost-benefit balance in favor of drug therapy in high-risk subjects."

What is claimed is:

1. A method for preventing or reducing the risk of a cardiovascular event which is angina in a patient who has one or more risk factors for a cornary event, which comprises administering to a patient in need of such treatment a therapeutically effective amount of pravastatin.

2. The method as defined in claim 1 wherein the patient to be treated has one or more risk factors which includes hypercholesterolemia, coronary artery disease, family history of coronary artery disease, hypertension, diabetes, cigarette smoking, cerebrovascular disease and/or male gender.

3. The method as defined in claim 1 wherein the patient to be treated has hypercholesterolemia.

4. The method as defined in claim 1 wherein treatment results in a reduction of onset of a cardiovascular event within one year of onset of treatment.

5. The method as defined in claim 1 wherein treatment results in a reduction of onset of a cardiovascular event within six months of onset of treatment.

6. The method as defined in claim 1 wherein pravastatin is administered in single or divided doses of from about 0.5 to about 2000 mg/one to four times daily.

* * * * *